(12) United States Patent
Jørsboe et al.

(10) Patent No.: US 6,372,477 B1
(45) Date of Patent: Apr. 16, 2002

(54) CLONING OF UDP-GALACTOSE EPIMERASE

(75) Inventors: Morten Jørsboe, Nykøbing F.; Janne Brunstedt, Roskide; Steen Guldager Petersen, Rodovre, all of (DK)

(73) Assignee: Danisco A/S, Copenhagen K (DK)

( * ) Notice: Subject to any disclaimer, the term of this patent is extended or adjusted under 35 U.S.C. 154(b) by 0 days.

(21) Appl. No.: 09/424,311
(22) PCT Filed: May 27, 1998
(86) PCT No.: PCT/IB98/00886
  § 371 Date: Jan. 24, 2000
  § 102(e) Date: Jan. 24, 2000
(87) PCT Pub. No.: WO98/54334
  PCT Pub. Date: Dec. 3, 1998

(30) Foreign Application Priority Data

May 28, 1997 (GB) .............................................. 9710991

(51) Int. Cl.[7] .............................. C12N 9/90; C12N 9/00; C12N 9/24; C12N 1/20; C12P 21/06
(52) U.S. Cl. ....................... 435/233; 435/69.1; 435/183; 435/200; 435/252.3; 435/320.1; 536/23.2; 800/295
(58) Field of Search .................................. 435/183, 200, 435/233, 252.3, 320.1, 69.1; 536/23.2; 800/295

(56) References Cited

PUBLICATIONS

Edwards et al. Biosynthesis of legume–seed galactomannans in vitro. Planta, vol. 178:41–51, 1989.*

* cited by examiner

*Primary Examiner*—Rebecca E. Prouty
*Assistant Examiner*—Manjunath Rao
(74) *Attorney, Agent, or Firm*—Foley & Lardner

(57) ABSTRACT

A UDP-galactose epimerase enzyme is described. In addition, there is described a nucleotide sequence coding for the same.

18 Claims, No Drawings

CLONING OF UDP-GALACTOSE EPIMERASE

The present invention relates to an enzyme. In addition, the present invention relates to a nucleotide sequence coding for the enzyme. The present invention also relates to one or more uses of the enzyme.

It is known that it is desirable to direct expression of a nucleotide sequence of interest ("NOI") in certain tissues of an organism, such as a filamentous fungus (e.g. *Aspergillus niger*) or even a plant crop. The resultant protein or enzyme may then be used in industry. Alternatively, the resultant protein or enzyme may be useful for the orgasm itself. For example it may be desirable to produce crop protein products with an optimised amino acid composition and so increase the nutritive value of a crop. For example, the crop may be made more useful as a feed. In the alternative, it may be desirable to isolate the resultant protein or enzyme and then use the protein or enzyme to prepare, for example, food compositions. In this regard, the resultant protein or enzyme can be a component of the food composition or it can be used to prepare food compositions including altering the characteristics or appearance of food compositions. It may even be desirable to use the organism such as a filamentous fungus or a crop plant, to express non-plant nucleotide sequences, such as for the same purposes.

The present invention seeks to provide an enzyme that is useful for industry and also a nucleotide sequence coding for same.

According to a first aspect of the present invention there is provided a UDP-galactose epimerase enzyme obtainable from guar.

According to a second aspect of the present invention there is provided a UDP-galactose epimerase enzyme obtainable from guar, wherein the enzyme comprises at least the sequence shown as SEQ ID No. 3 or SEQ ID No. 4, or a variant homologue or fragment thereof.

According to a third aspect of the present invention there is provided a UDP-galactose epimerase enzyme obtainable from guar, wherein the enzyme is encoded by a nucleotide sequence that comprises at least the sequence shown as SEQ ID No. 1 or SEQ ID No. 2, or a variant, homologue or fragment thereof.

According to a fourth aspect of the present invention there is provided a nucleotide sequence that comprises at least the sequence shown as SEQ ID No. 1 or SEQ ID No. 2, or a variant, homologue or fragment thereof, or a sequence complementary thereto.

According to a fifth aspect of the present invention there is provided a UDP-galactose epimerase enzyme which is immunologically reactive with an antibody raised against a purified UDP-galactose epimerase enzyme according to the present invention.

According to a sixth aspect of the present invention there is provided a process of preparing an enzyme according to the present invention comprising expressing a nucleotide sequence according to the present invention.

According to a seventh aspect of the present invention there is provided the use of an enzyme according to the present invention or an enzyme prepared by a process according to the present invention to prepare a foodstuff (such as a feed).

According to an eighth aspect of the present invention there is provided a nucleotide sequence according to the present invention operatively linked to a promoter.

According to a ninth aspect of the present invention there is provided a foodstuff comprising or prepared from the enzyme according to the present invention or an enzyme prepared by a process according to the present invention.

Other aspects of the present invention include: a construct comprising or capable of expressing the present invention; a vector comprising or capable of expressing the present invention; a plasmid comprising or capable of expressing the present invention: a tissue comprising or capable of expressing the present invention; an organ comprising or capable of expressing the present invention; a transgenic organism comprising or capable of expressing the present invention.

Preferably the enzyme comprises the sequence shown as SEQ. I.D. No. 3 or SEQ. ID No. 4, or a variant, homologue or fragment thereof, and the nucleotide sequence encoding same comprises the sequence shown as SEQ. I.D. No. 1 or SEQ ID No. 2 or a variant, homologue or fragment thereof.

Other aspects of the present invention include methods of expressing or allowing the expression of or transforming any one of the nucleotide sequence, the construct, the plasmid, the vector, the cell, the tissue, the organ or the organism, as well as the products thereof.

Further aspects of the present invention include uses of the enzyme for preparing or treating foodstuffs, including animal feed.

Some of the key advantages of the present invention are that it provides an enzyme having UDP-galactose epimerase activity. UDP-galactose epimerase is an important enzyme as inter alia it catalyses the conversion of UDP-D-glucose to UDP-D-galactose. In addition, the enzyme of the present invention may be prepared in certain or specific cells or tissues, such as in just a specific cell or tissue, of an organism, such as a plant or, by way of possible further example, a microorganism. The present invention also provides a nucleotide sequence coding for the enzyme UDP-galactose epimerase that may be expressed preferably in specific cells or tissues, such an those of an organism, such as a plant or, by way of possible further example, a microorganism.

Also, the present invention provides constructs, vectors, plasmids, cells, tissues, organs and organisms comprising the nucleotide sequence according to the present invention and methods of expressing the same, preferably in specific cells or tissues, such as expression in just a specific cell or tissue, of an organism such as a plant or, by way of possible further example, a microorganism.

Preferably, the enzyme of the present invention is used in the preparation of a foodstuff. Typical foodstuffs may include dairy products, meat products, poultry products, fish products and bakery products.

The terms "variant", "homologue" or "fragment" in relation to the amino acid sequence for the preferred UDP-galactose epimerase enzyme of the present invention include any substitution of, variation of, modification of, replacement of, deletion of or addition of one (or more) amino acid from or to the sequence providing the resultant enzyme has UDP-galactose epimerase activity, preferably having at least the same activity of the enzyme comprising the sequence shown as SEQ ID No. 3 or SEQ ID No. 4. In particular, the term "homologue" covers homology with respect to structure and/or function. With respect to sequence homology, preferably there is at least 75%, more preferably at least 85%, more preferably at least 90% homology to an enzyme comprising the sequence shown as SEQ ID No. 3 or SEQ ID No. 4. More preferably there is at least 95%, more preferably at least 98%, homology to an enzyme comprising the sequence shown as SEQ ID No. 3 or SEQ ID No. 4.

The terms "variant", "homologue" or "fragment" in relation to the nucleotide sequence coding for the UDP-galactose epimerase enzyme of the present invention include any substitution of, variation of, modification of, replacement of, deletion of or addition of one (or more), nucleic acid from or to the sequence providing the resultant nucleotide sequence codes for or is capable of coding for an enzyme having UDP-galactose epimerase activity, preferably having at least the same activity of the enzyme comprising the sequence shown as SEQ ID No. 1 or SEQ ID No. 2. In particular, the term "homologue" covers homology with respect to structure and/or function providing the resultant nucleotide sequence codes for or is capable of coding for an enzyme having UDP-galactose epimerase activity. With respect to sequence homology, preferably there is at least 75%, more preferably at least 85%, more preferably at least 90% homology to a sequence comprising the sequence shown as SEQ ID No. 1 or SEQ ID No. 2. More preferably there is at, least 95%, more preferably at least 98%, homology to a sequence that comprises the sequence shown as SEQ ID No. 1 or SEQ ID No. 2.

The above terms are synonymous with allelic variations of the sequences.

The present invention also covers sequences that are complementary to the above-mentioned nucleotide sequences. The term "complementary" means that the present invention covers nucleotide sequences that can hybridise to the nucleotide sequence of the present invention as defined above, preferably under stringent hybridisation conditions.

The term "nucleotide" in relation to the present invention includes genomic DNA, cDNA, synthetic DNA, and RNA. Preferably it means DNA, more preferably it means cDNA.

The term "construct"—which is synonymous with terms such as "conjugate", "cassette" and "hybrid"—includes the nucleotide sequence according to the present invention directly or indirectly attached to a promoter. An example of an indirect attachment is the provision of a suitable spacer group such as an intron sequence, such as the Sh1-intron or the ADH intron, intermediate the promoter and the nucleotide sequence of the present invention. The same is true for the term "fused" in relation to the present invention which includes direct or indirect attachment. In each case, the terms do not cover the natural combination of the nucleotide sequence coding for the enzyme ordinarily associated with the wild type gene promoter and when they are both in their natural environment. A highly preferred embodiment is the nucleotide sequence according to the present invention is operably linked to a promoter.

The construct may even contain or express a marker which allows for the selection of the genetic construct in, for example, a filamentous fungus, preferably of the genus Aspergillus, such as *Aspergillus niger*, or plants, such as potatoes, sugar beet etc., into which it has been transferred. Alternatively, or in addition, the construct may even contain or express a marker which allows for the selection of the genetic construct in, for example, a plant seed, such as corn, wheat or barley, into which it has been transferred. Various markers exist which may be used, such as for example those encoding mannose6-phosphate isomerase (especially for plants) or those markers that provide for antibiotic resistance—e.g. resistance to G418, hygromycin, bleomycin, kanamycin and gentamycin.

The term "vector" includes expression vectors and transformation vectors.

The term "expression vector" means a construct capable of in vivo or in vitro expression.

The term "transformation vector" means a construct capable of being transferred from one species to another—such as from an *E.coli* plasmid to a filamentous fungus, preferably of the genus Aspergillus. It may even be a construct capable of being transferred from an *E. coli* plasmid to an Agrobacterium to a plant.

The term "tissue" includes isolated tissue and tissue within an organ.

The term "organism" in relation to the present invention includes any organism that could comprise the nucleotide sequence coding for the enzyme according to the present invention and/or the expression product obtained therefrom, wherein nucleotide sequence according to the present invention can be expressed when present in the organism.

The organism may be a plant.

The organism may be a filamentous fungus, preferably of the genus Aspergillus, more preferably *Aspergillus niger*.

Other preferred organisms include any suitable other microorganisms, such as one of Bacillus, *Aspergillus oryzae, A. tubigensis, A. awamori, Trichoderma reesei, T. viride* and *T. longibrachiatum*.

The term "transgenic organism" in relation to the present invention includes any organism that comprises the nucleotide sequence coding for the enzyme according to the present invention and/or the expression product obtained therefrom, wherein the nucleotide sequence according to the present invention can be expressed within the organism. Preferably the nucleotide sequence is incorporated in the genome of the organism.

Therefore, the transgenic organism of the present invention includes an organism comprising any one of, or combinations of, the nucleotide sequence coding for the enzyme according to the present invention, constructs according to the present invention, vectors according to the present invention, plasmids according to the present invention, cells according to the present invention, tissues according to the present invention or the products thereof. For example the transgenic organism can also comprise the nucleotide sequence coding for the enzyme of the present invention under the control of a promoter.

The term "transgenic organism" does not cover the native nucleotide coding sequence according to the present invention in its natural environment when it is under the control of its native promoter which is also in its natural environment. In addition, the present invention does not cover the native enzyme according to the present invention when it is in its natural environment and when it has been expressed by its native nucleotide coding sequence which is also in its natural environment and when that nucleotide sequence is under the control of its native promoter which is also in its natural environment.

The transformed cell or organism could prepare acceptable quantities of the desired expression product which would be easily retrievable from, the cell or organism.

Preferably the construct of the present invention comprises the nucleotide sequence of the present invention and a promoter. The term "promoter" is used in the normal sense of the art, e.g. an RNA polymerase binding site in the Jacob-Monod theory of gene expression.

By way of example, the promoter for the nucleotide sequence of the present invention may be the α-Amy 1 promoter (otherwise known as the Amy 1 promoter, the Amy 637 promoter or the α-Amy 637 promoter) as described in PCT patent application PCT/EP95/02195 (incorporated herein by reference). Alternatively, the promoter for the nucleotide sequence of the present invention can be the α-Amy 3 promoter (otherwise known as the Amy 3 promoter, the Amy 351 promoter or the α-Amy 351 promoter) as described in PCT patent application PCT/

EP95/02196 (incorporated herein by reference). Alternatively, the promoter could be the glucanase promoter—sometimes referred to as the egla promoter—as described in PCT patent application PCT/EP96/01008 (incorporated herein by reference). Alternatively, the promoter could be the arabinofilranosidase promoter as described in PCT patent application PCT/EP96/01009 (incorporated herein by reference).

In addition to the nucleotide sequences described above, the promoter for use in expressing the nucleotide sequence according to the present invention could additionally include features to ensure or to increase expression in a suitable host. For example, the features can be conserved regions such as a Pribnow Box or a TATA box. The promoters may even contain other sequences to affect (such as to maintain, enhance, decrease) the levels of expression of the nucleotide sequence according to the present invention. For example, suitable other sequences include the Sh1-intron or an ADH intron. Other sequences include inducible elements—such as temperature, chemical, light or stress inducible elements. Also, suitable elements to enhance transcription or translation may be present. An example of the latter element is the TMV 5' signal sequence (see Sleat Gene 217 [1987] 217–225; and Dawson Plant Mol. Biol. 23 [1993]97).

The present invention also encompasses combinations of promoters and/or nucleotide sequences coding for proteins or recombinant enzymes and/or elements.

The present invention also encompasses the use of promoters to express a nucleotide sequence coding for the enzyme according to the present invention, wherein a part of the promoter is inactivated but wherein the promoter can still function as a promoter. Partial inactivation of a promoter in some instances is advantageous. In particular, with the Amy 351 promoter mentioned earlier it is possible to inactivate a part of it so that the partially inactivated promoter expresses the nucleotide of the present invention in a more specific manner such as in just one specific tissue type or organ.

The term "partial inactivation" means that the expression pattern of the promoter is modified but wherein the partially inactivated promoter still functions as a promoter. However, as mentioned above, the modified promoter is capable of expressing the nucleotide of the present invention in at least one (but not all) specific tissue of the original promoter. One such promoter is the Amy 351 promoter described above. Examples of partial inactivation include altering the folding pattern of the promoter sequence, or binding species to pans of the nucleotide sequence, so that a part of the nucleotide sequence is not recognised by, for example, RNA polymerase. Another, and preferable, way of partially inactivating the promoter is to truncate it to form fragments thereof. Another way would be to mutate at least a part of the sequence so that the RNA polymerase can not bind to that part or another part. Another modification is to mutate the binding sites for regulatory proteins for example the CreA protein known from filamentous fungi to exert carbon catabolite repression, and thus abolish the catabolite repression of the native promoter.

The nucleotide sequence of the present invention may be expressed before, during or after the expression of another NOI. Here the other NOI can be any suitable nucleotide sequence (or sequences) of interest. The other NOI can be any nucleotide that is either foreign or natural to the organism (e.g. Filamentous fungus, preferably of the genus Aspergillus, or a plant) in question. Typical examples of other NOIs include nucleotide sequences encoding proteins and enzymes that modify metabolic and catabolic processes.

The other NOI may code for an agent for introducing or increasing pathogen resistance. The other NOI may even be an antisense construct for modifying the expression of natural transcripts present in the relevant tissues. The other NOI may even code for a non-native protein of a filamentous fungus or a compound that is of benefit to animals or humans. Examples of other NOIs include pectinases, pectin depolymerases, polygalacturonases, pectate lyases, pectin lyases, rhamno-galacturonases, hemicellulases, endo-β-glucanases, arabinases, or acetyl esterases, or combinations thereof, as well as antisense sequences thereof. The other NOI may be a protein giving nutritional value to a food or crop. Typical examples include plant proteins that can inhibit the formation of anti-nutritive factors and plant proteins that have a more desirable amino acid composition (e.g. a higher lysine content than a non-transgenic plant).

The other NOI may even code for an enzyme that can be used in food processing such as chymosin, thaumatin and α-galactosidase. The other NOI can be a nucleotide sequence encoding any one of a pest toxin, an antisense transcript such as that for patatin or α-amylase, ADP-glucose pyrophosphorylase (e.g. see EP-A-0455316), a protease enzyme, a glucanase or genomic β-1,4-endoglucanase.

The other NOI can be the nucleotide sequence coding for the arabinofuranosidase enzyme which is the subject of PCT patent application PCT/EP96/01009 (incorporated herein by reference). The other NOI can be any of the nucleotide sequences coding for the ADP-glucose pyrophosphorylase enzymes which are the subject of PCT patent application PCT/EP94/01082 (incorporated herein by reference). The other NOI can be any of the nucleotide sequences coding for the α-glucan lyase enzyme which are described in PCT patent application PCT/EP94/03397 (incorporated herein by reference). The other NOI can be any of the nucleotide sequences coding for the glucanase enzyme which are described in PCT patent application PCT/EP96/01008 (incorporated herein by reference).

The host organism can be a prokaryotic or a eukaryotic organism. Examples of suitable prokaryotic hosts include *E. coli* and *Bacillus subtilis*. Teachings on the transformation of prokaryotic hosts is well documented in the art, for example see Sambrook et al (Molecular Cloning: A Laboratory Manual, 2nd edition, 1989, Cold Spring Harbor Laboratory Press). If a prokaryotic host is used then the nucleotide sequence may need to be suitably modified before transformation—such as by removal of introns.

Preferably, in any one of the plasmid, the vector such as an expression vector or a transformation vector, the cell, the tissue, the organ, the organism or the transgenic organism, the promoter is present in combination with at least one NOI.

Preferably the promoter and the NOI are stably maintained within the transgenic organism. By way of example, the promoter and the NOI (such as at least the nucleotide sequence according to the present invention) may be maintained within the transgenic organism in a stable extrachromosomal construct. This is preferred for transgenic bacteria and yeast, or even some filamentous fungi. Alternatively, the promoter and the NOI (such as at least the nucleotide sequence according to the present invention) may be stably incorporated within the transgenic organism's genome. This is preferred for some transgenic bacteria and yeast, and most filamentous fungi.

A possible preferred transgenic organism is a filamentous fungus, preferably of the genus Aspergillus, more preferably *Aspergillus niger*. Alternatively, the transgenic organism can be a yeast. The transgenic organism can even be a plant, such as a monocot or dicot plant.

A possible preferred host organism for the expression of the nucleotide sequence of the present invention and/or for the preparation of the enzyme according to the present invention is an organism of the genus Aspergillus, such as *Aspergillus niger*. In this regard, a transgenic Aspergillus according to the present invention can be prepared by following the teachings of Rambosek, J. and Leach, 1987 (Recombinant DNA in filamentous fungi: Progress and Prospects. CRC Crit. Rev. Biotechnol. 6:357–393), Davis R. W. 1994 (Heterologous gene expression and protein secretion in Aspergillus. In: Martinelli S. D., Kinghorn J. R. (Editors) Aspergillus: 50 years on. Progress in industrial microbiology vol 29. Elsevier Amsterdam 1994. pp 525–560), Ballance, D. J. 1991 (Transformation systems for Filamentous Fungi and an Overview of Fungal Gene structure. In: Leong, S. A., Berka R. M. (Editors) Molecular Industrial Mycology. Systems and Applications for Filamentous Fungi. Marcel Dekker Inc. New York 1991. pp 1–29) and Turner G. 1994 (Vectors for genetic manipulation. In: Martinelli S. D., Kinghorn J. R.( Editors) Aspergillus: 50 years on. Progress in industrial microbiology vol 29.

Elsevier Amsterdam 1994. pp. 641–666). The following commentary provides a summary of those teachings for producing transgenic Aspergillus according to the present invention.

For almost a century, filamentous fungi have been widely used in many types of industry for the production of organic compounds and enzymes. For example, traditional Japanese koji and soy fermentations have used Aspergillus sp. Also, in this century *Aspergillus niger* has been used for production of organic acids particular citric acid and for production of various enzymes for use in industry.

There are two major reasons why filamentous fungi have been so widely used in industry. First filamentous fungi can produce high amounts of extracellular products, for example enzymes and organic compounds such as antibiotics or organic acids. Second filamentous fungi can grow on low cost substrates such as grains, bran, beet pulp etc. The same reasons have made filamentous fungi attractive organisms as hosts for heterologous expression according to the present invention.

In order to prepare the transgenic Aspergillus, expression constructs are prepared by inserting a NOI into a construct designed for expression in filamentous fungi.

Several types of constructs used for heterologous expression have been developed. The constructs contain a promoter and the NOI which is active in fungi. Examples of promoters include a fungal promoter for a highly expressed extracellular enzyme, such as the glucoamylase promoter or the α-amylase promoter. The NOI can be fused to a signal sequence which directs the protein encoded by the NOI to be secreted. Usually a signal sequence of fungal origin is used. A terminator active in fungi ends the expression system.

Another type of expression system has been developed in fungi where the nucleotide sequence according to the present invention is fused to a smaller or a larger part of a fungal nucleotide sequence encoding a stable protein. This aspect can stabilize the protein encoded by the nucleotide sequence according to the present invention. In such a system a cleavage site, recognized by a specific protease, can be introduced between the fungal protein and the protein encoded by the nucleotide sequence according to the present invention (or even another NOI), so the produced fusion protein can be cleaved at this position by the specific protease thus liberating the protein encoded by the nucleotide sequence according to the present invention (or even another NOI). By way of example, one can introduce a site which is recognized by a KEX-2 like peptidase found in at least some Aspergilli (Broekhuijsen et al 1993 J Biotechnol 31 135–145). Such a fusion leads to cleavage in vivo resulting in production of the expressed product and not a larger fusion protein.

Heterologous expression in Aspergillus has been reported for several nucleotide sequences encoding bacterial, fungal, vertebrate and plant proteins. The proteins can be deposited intracellularly if the nucleotide sequence according to the present invention (or another NOI) is not fused to a signal sequence. Such proteins will accumulate in the cytoplasm and will usually not be glycosylated which can be an advantage for some bacterial proteins. If the nucleotide sequence according to the present invention (or another NOI) is equipped with a signal sequence the protein will accumulate extracellularly.

With regard to product stability and host strain modifications, some heterologous proteins are not very stable when they are secreted into the culture fluid of fungi. Most fungi produce several extracellular proteases which degrade heterologous proteins. To avoid this problem special fungal strains with reduced protease production have been used as host for heterologous production.

For the transformation of filamentous fungi, several transformation protocols have been developed for many filamentous fungi (Ballance 1991, ibid). Many of them are based on preparation of protoplasts and introduction of DNA into the protoplasts using PEG and $Ca^{2+}$ ions. The transformed protoplasts then regenerate and the transformed fungi are selected using various selective markers. Among the markers used for transformation are a number of auxotrophic markers such as argB, trpC, niaD and pyrG, antibiotic resistance markers such as benomyl resistance, hygromycin resistance and phleomycin resistance. A commonly used transformation marker is the amdS gene of *A. nidulans* which in high copy number allows the fungus to grow with acrylamide as the sole nitrogen source.

In another embodiment the transgenic organism can be a yeast. In this regard, yeast have also been widely used as a vehicle for heterologous gene expression. The species *Saccharomyces cerevisiae* has a long history of industrial use, including its use for heterologous gene expression. Expression of heterologous nucleotide sequences in *Saccharomyces cerevisiae* has been reviewed by Goodey et al (1987, Yeast Biotechnology, D R Berry et al, eds, pp 401–429, Allen and Unwin, London) and by King et al (1989, Molecular and Cell Biology of Yeasts, E F Walton and G T Yarronton, eds, pp 107–133, Blackie, Glasgow).

For several reasons *Saccharomyces cerevisiae* is well suited for heterologous nucleotide sequence expression. First, it is non-pathogenic to humans and it is incapable of producing certain endotoxins. Second, it has a long history of safe use following centuries of commercial exploitation for various purposes. This has led to wide public acceptability. Third, the extensive commercial use and research devoted to the organism has resulted in a wealth of knowledge about the genetics and physiology as well as large-scale fermentation characteristics of *Saccharomyces cerevisiae*.

A review of the principles of heterologous gene expression in *Saccharomyces cerevisiae* and secretion of gene products is given by E Hinchcliffe E Kenny (1993, "Yeast as a vehicle for the expression of heterologous genes", Yeasts, Vol 5, Anthony H Rose and J Stuart Harrison, eds, 2nd edition, Academic Press Ltd.).

Several types of yeast vectors are available, including integrative vectors, which require recombination with the host genome for their maintenance, and autonomously replicating plasmid vectors.

In order to prepare the transgenic Saccharomyces, expression constructs are prepared by inserting the nucleotide sequence of the present invention into a construct designed for expression in yeast. Several types of constructs used for heterologous expression have been developed. The constructs contain a promoter active in yeast fused to the nucleotide sequence of the present invention, usually a promoter of yeast origin, such as the GAL1 promoter, is used. Usually a signal sequence of yeast origin, such as the sequence encoding the SUC2 signal peptide, is used. A terminator active in yeast ends the expression system.

For the transformation of yeast several transformation protocols have been developed. For example, a transgenic Saccharomyces according to the present invention can be prepared by following the teachings of Hinnen et al (1978, Proceedings of the National Academy of Sciences of the USA 75, 1929); Beggs, J D (1978, Nature, London, 275, 104); and Ito, H et al (1983, J Bacteriology 153, 163–168).

The transformed yeast cells are selected using various selective markers. Among the markers used for transformation are a number of auxotrophic markers such as LEU2, HIS4 and TRP1, and dominant antibiotic resistance markers such as aminoglycoside antibiotic markers, eg G418.

Another host organism is a plant. Even though the enzyme and the nucleotide sequence coding therefor are not disclosed in EP-B-0470145 and. CA-A-2006454, those two documents do provide some useful background commentary on the types of techniques that may be employed to prepare transgenic plants according to the present invention. Some of these background teachings are now included in the following commentary.

The basic principle in the construction of genetically modified plants is to insert genetic information in the plant genome so as to obtain a stable maintenance of the inserted genetic material.

Several techniques exist for inserting the genetic information, the two main principles being direct introduction of the genetic information and introduction of the genetic information by use of a vector system. A review of the general techniques may be found in articles by Potrykus (Annu Rev Plant Physiol Plant Mol Biol [1991] 42:205–225) and Christou (Agro-Food-Industry Hi-Tech March/April 1994 17–27).

Thus, in one aspect, the present invention relates to a vector system which carries a nucleotide sequence or construct according to the present invention and which is capable of introducing the nucleotide sequence or construct into the genome of an organism, such as a plant.

The vector system may comprise one vector, but it can comprise two vectors. In the case of two vectors, the vector system is normally referred to as a binary vector system. Binary vector systems are described in further detail in Gynheung An et al. (1980), Binary Vectors, *Plant Molecular Biology Manual* A3, 1–19.

One extensively employed system for transformation of plant cells with a given nucleotide sequence or construct is based on the use of a Ti plasmid from *Agrobacterium tumefaciens* or a Ri plasmid from *Agrobacterium rhizogenes* An et al. (1986), *Plant Physiol.* 81, 301–305 and Butcher D. N. et al. (1980), *Tissue Culture Methods for Plant Pathologists*, eds.: D. S. Ingrams and J. P. Helgeson, 203–208. Several different Ti and Ri plasmids have been constructed which are suitable for the construction of the plant or plant cell constructs described above. A non-limiting example of such a Ti plasmid is pGV3850.

The nucleotide sequence or construct of the present invention should preferably be inserted into the Ti-plasmid between the terminal sequences of the T-DNA or adjacent a T-DNA sequence so as to avoid disruption of the sequences immediately surrounding the T-DNA borders, as at least one of these regions appear to be essential for insertion of modified T-DNA into the plant genome.

As will be understood from the above explanation, if the organism is a plant, then the vector system of the present invention is preferably one which contains the sequences necessary to infect the plant (e.g. the vir region) and at least one border part of a T-DNA sequence, the border part being located on the same vector as the genetic construct.

Preferably, the vector system is an *Agrobacterium tumefaciens* Ti-plasmid or an *Agrobacterium rhizogenes* Ri-plasmid or a derivative thereof, as these plasmids are well-known and widely employed in the construction of transgenic plants, many vector systems exist which are based on these plasmids or derivatives thereof.

In the construction of a transgenic plant the nucleotide sequence or construct of the present invention may be first constructed in a microorganism in which the vector can replicate and which is easy to manipulate before insertion into the plant. An example of a useful microorganism is *E. coli*, but other microorganisms having the above properties may be used. When a vector of a vector system as defined above has been constructed in *E. coli.* it is transferred, if necessary, into a suitable Agrobacterium strain, e.g. *Agrobacterium tumefaciens*. The Ti-plasmid harbouring the nucleotide sequence or construct of the invention is thus preferably transferred into a suitable Agrobacterium strain, e.g. A. tumefaciens, so as to obtain an Agrobacterium cell harbouring the nucleotide sequence or construct of the invention, which DNA is subsequently transferred into the plant cell to be modified.

As reported in CA-A-2006454, a large amount of cloning vectors are available which contain a replication system in *E. coli* and a marker which allows a selection of the transformed cells. The vectors contain for example pBR 322, the pUC series, the M13 mp series, pACYC 184 etc.

In this way, the nucleotide sequence or construct of the present invention can be introduced into a suitable restriction position in the vector. The contained plasmid is used for the transformation in *E.coli*. The *E.coli* cells are cultivated in a suitable nutrient medium and then harvested and lysed. The plasmid is then recovered and then analysed—such as by any one or more of the following techniques: sequence analysis, restriction analysis, electrophoresis and further biochemical-molecular biological methods. After each manipulation, the used DNA sequence can be restricted and connected with the next DNA sequence. Each sequence can be cloned in the same or different plasmid.

After each introduction method of the desired construct or nucleotide sequence according to the present invention in the plants the presence and/or insertion of further DNA sequences may be necessary. If, for example, for the transformation the Ti- or Ri-plasmid of the plant cells is used, at least the right boundary and often however the right and the left boundary of the Ti- and Ri-plasmid T-DNA, as flanking areas of the introduced nucleotide sequences, can be connected. The use of T-DNA for the transformation of plant cells has been intensively studied and is described in EP-A-120516; Hoekema, in: The Binary Plant Vector System Offset-drukkerij kanters B. B., Alblasserdam, 1985, Chapter V; Fraley, et al., Crit. Rev. Plant Sci., 4:1–46 ; and An et al., EMBO J. (1985) 4:277–284.

Direct infection of plant tissues by Agrobacterium is a simple technique which has been widely employed and which is described in Butcher D. N. et al. (1980), *Tissue*

Culture Methods for Plant Pathologists, eds.: D. S. Ingrams and J. P. Helgeson, 203–208. For further teachings on this topic see Potrykus (Annu Rev Plant Physiol Plant Mol Biol [1991] 42:205–225) and Christou (Agro-Food-Industry Hi-Tech March/April 1994 17–27). With this technique, infection of a plant may be done on a certain part or tissue of the plant, i.e. on a part of a leaf, a root, a stem or another part of the plant.

Typically, with direct infection of plant tissues by Agrobacterium carrying the promoter and the NOI, a plant to be infected is wounded, e.g. by cutting the plant with a razor or puncturing the plant with a needle or rubbing the plant with an abrasive. The wound is then inoculated with the Agrobacterium. The inoculated plant or plant part is then grown on a suitable culture medium and allowed to develop into mature plants.

When plant cells are constructed, these cells may be grown and maintained in accordance with well-known tissue culturing methods such as by culturing the cells in a suitable culture medium supplied with the necessary growth factors such as amino acids, plant hormones, vitamins, etc. Regeneration of the transformed cells into genetically modified plants may be accomplished using known methods for-the regeneration of plants from cell or tissue cultures, for example by selecting transformed shoots using an antibiotic and by subculturing the shoots on a medium containing the appropriate nutrients, plant hormones, etc.

Further teachings on plant transformation may be found in EP-A-0449375.

In summation, the present invention provides a UDP-galactose epimerase enzyme and a nucleotide sequence coding for the same.

The following samples were deposited in accordance with the Budapest Treaty at the recognised depositary The National Collections of Industrial and Marine Bacteria Limited (NCIMB) at 23 St. Machar Drive, Aberdeen, Scotland, United Kingdom, AB2 1RY on 23 May 1997:

1. *E.coli* DH5αpGEPI42. The deposit number is NCIMB 40881. NCIMB 40881 contains clone GEPI42—which comprises SEQ ID No. 1.
2. *E.coli* DH5αpGEPI48. The deposit number is NCIMB 40982. NCIMB 40882 contains clone GEPI48—which comprises SEQ ID No. 2.

Highly preferred aspects of the present invention therefore relate to nucleotide coding sequences obtainable from those deposits, including expression vectors, constructs, organisms and transgenic organisms coupling those same sequences or plasmids.

Thus, according to a preferred embodiment the nucleotide sequence of the present invention is obtainable from deposit number NCIMB 40881 or NCIMB 40882, or is a variant, homologue or fragment thereof.

According to a more preferred embodiment the nucleotide sequence of the present invention is obtainable from deposit number NCIMB 40881 or NCIMB 40882.

The present invention will now be described only by way of example.

Cloning and Partial Characterization of UDP-galactose Epimerase Nucleotide Sequences from Guar (*Cyamopsis tetragonoloba*)

Biochemical studies on UDP-galactose 4-epimerase (EC 5.1.3.2.) in guar have shown that even though fairly high activity of this enzyme is found, the amount of UDP-galactose epimerase protein was very small preventing preparative purification for amino acid analysis. Therefore, the cloning strategy of choice was by functional complementation in an galE—*E. coli* mutant.

cDNA Library

A cDNA expression library representing mRNA from immature guar seeds was constructed in the plasmid pcDNAII (Invitrogen Corporation) and transformed into the *E. coli* strain Top10F'. The quality of the cDNA library was controlled by purification of plasmids from a number of separate Top10F' colonies, picked at random. Restriction enzyme analysis revealed that all examined plasmids were recombinant.

UDP-Galactose Epimerase Deficient *E. coli* Strain

The *E. coli* strain PL-2 is not able to metabolise galactose due to a defective galE- gene while the two other genes of the gal-operon, galK and galT, are intact (Buttin, J Mol Diol, 7, 164–182 (1963); Wu and Kalckar, Proc Nat Acad Sci, USA 55, 622–629 (1966). Thus, insertion of an active UDP-galactose epimerase gene in PL-2 would allow this strain to grow on galactose.

Transformation of PL2 and Selection

PL-2 cells were made competent by the method of Hanahan (Techniques for transformation of *E. coli*. IRL Press, Oxford (ISBN 0-947946-18-17), 109–135 (1985). A titer of $5 \times 10^6$ transformed cells/µg library plasmid was obtained.

The selection medium was essentially a minimal medium added galactose, consisting of M9 salts (Maniatis et al, Molecular cloning, a laboratory manual, Cold Spring Harbor, N.Y. (ISBN 0-87969-136-0)) (1982) and added 0.05 1 threonine, 0.05 g/l leucine, 0.05 g/l methionine, 1.0 g/l of thiamin-HC1, 50 mg/l ampicillin, 0.8 g/l fructose, 0.9 g/l agarose and 6 or 8 g/l galactose. The media are hereafter called M9-ES6 (containing 6 g/l galactose) or M9-ES8 (containing 8 g/l galactose).

Competent PL-2 cells were transformed with the guar cDNA library and cells were plated onto the selective substrate M9-ES6 or M9-ES8. After two days at 37° C., colonies appeared (approx 0.1% of the total number of transformants). A total of 48 colonies were selected.

UDP-galactose Epimerase Assay on Selected Colonies

In order to establish whether the acquired ability to grow on galactose was due to the presence of UDP-galactose activity, all selected colonies were tested for UDP-galactose epimerase activity using crude extracts produced by sonication and subsequent clarification by centrifugation. The UDP-galactose epimerase assays were performed essentially according to Dey (Phytochem, 23, 729–732 (1984)). The UDP-galactose epimerase activity in extracts of PL-2 was zero (negative control) while significant levels of activity was found in DH5a (positive control), as expected. Transformed PL-2 colonies displaying high levels of UDP-galactose epimerase activity were chosen for further analysis.

Retransformation with Plasmid DNA from Colonies 42 and 48

Plasmids from colony 42 and colony 48 were purified and retransformed into competent PL-2 cells and plated on M9-ES6 or M9-ES8. In both retransformation experiments, a large number of colonies appeared after two days at 37° C. About ten independent colonies from each were analysed for UDP-galactose epimerase activity and all extracts contained similar high levels of UDP-galactose activity as found in the original colonies 42 and 48. This experiment demonstrates that the UDP-galactose epimerase activity detected in the PL-2 derived colonies 42 and 48 is encoded by the cDNA inserts.

DNA Sequencing Analysis of the Inserts in Colonies 42 and 48

Partial nucleotide sequences of the UDP-galactose4-epimerase containing clones, pGEPI42 and pGEPI48, were determined using a Termo sequenase fluorescent cycle sequencing kit (Amersham) and an ALF DNA sequencer (Pharmacia).

Sequence ID No. 1 and No. 2 show partial nucleotide sequences of the inserts in colonies 42 and 48, respectively, along with the deduced amino acid sequences.

Antibody Production

Antibodies were raised against the enzyme of the present invention by injecting rabbits with the purified enzyme and isolating the immunoglobulins from antiserum according to procedures described according to N Harboe and A Ingild ("Immunization, Isolation of Immunoglobulins, Estimation of Antibody Titre" In A Manual of Quantitative Immunoelectrophoresis, Methods and Applications, N H Axelsen, et al (eds.), Universitetsforlaget, Oslo, 1973) and by T G Cooper ("The Tools of Biochemistry", John Wiley & Sons, New York, 1977).

Other modifications of the present invention will be apparent to those skilled in the art.

---

\* TRANSLATION OF A NUCLEIC ACID SEQUENCE \*

Done on DNA sequence GEPI42.
Total number of bases is: 381.

```
          10        20        30        40        50        60
          |         |         |         |         |         |
GAATTCCTGAAATCTGAAGTGTGAAGAAGAATAATAATAAGGAACAGTGAGTGGGATTTG 70        80        90       100       110       120
          |         |         |         |         |         |
AAGGGAAAGAAGAAGAAGAAGAAGATGGTGTCGTCGAGGATGGCGTCAGGGGAAACAATT
                                M  V  S  S  R  M  A  S  G  E  T  I 130       140       150       160       170       180
          |         |         |         |         |         |
CTGGTAACTGGAGGAGCTGGATTCATCGGATCTCACACGGTGGTTCAGCTTCTGAAGCAA
 L  V  T  G  G  A  G  F  I  G  S  H  T  V  V  Q  L  L  K  Q 190       200       210       220       230       240
          |         |         |         |         |         |
GGGTTTCACGTATCCATCATCGACAATCTCTACAACTCCGTCATCGACGCCGTCCATAGG
 G  F  H  V  S  I  I  D  N  L  Y  N  S  V  I  D  A  V  H  R 250       260       270       280       290       300
          |         |         |         |         |         |
GTTCGCCTTTTGGTGGGTCCACTCCTCTCCAGCAACCTCCATTTCCATCACGGCGACCTC
 V  R  L  L  V  G  P  L  L  S  S  N  L  H  F  H  H  G  D  L 310       320       330       340       350       360
          |         |         |         |         |         |
CGCAACATCCATGACCTCGACATCCTCTTCTCTAAAACCAAATTTGATGCCGTGATCCAA
 R  N  I  H  D  L  D  I  L  F  S  K  T  K  F  D  A  V  I  Q 370       380
          |         |
CTTGCGGGCCCCAAAGGTGTG
 L A  G  P  K  G  V
```

SEQ ID NO. 1

---

\* TRANSLATION OF A NUCLEIC ACID SEQUENCE \*

Done on DNA sequence GEPI48.
Total number of bases is: 351.

```
          10        20        30        40        50        60
          |         |         |         |         |         |
GAATTCCTTCAAAGCTATCCATACCGCTTACGCATTCATTCACTCCACCTTCTCTTTCTC 70        80        90       100       110       120
          |         |         |         |         |         |
TCTCAGCTCCCTTCAATTATGTCATCCCAAACGGTTCTCGTCACCGGCGGAGCCGGTTAC
                          M  S  S  Q  T  V  L  V  T  G  G  A  G  Y 130       140       150       160       170       180
          |         |         |         |         |         |
ATCGGCAGCCACACCGTCCTTCAGCTTCTCCTCGGTGGTTTCAAGGCCGTTGTCGTTGAC
 I  G  S  H  T  V  L  Q  L  L  L  G  G  F  K  A  V  V  V  D
```

```
                    * TRANSLATION OF A NUCLEIC ACID SEQUENCE *

190       200       210       220       230       240
          |         |         |         |         |         |
    AACCTCGATAATTCTTCCGAGACCGCCATCCACAGAGTCAAGGAACTCGCCGGTAAATTC
     N  L  D  N  S  S  E  T  A  I  H  R  V  K  E  L  A  G  K  F 250       260       270       280       290       300
          |         |         |         |         |         |
    GCCGGTAATCTCTCCTTTCACAAGTTAGACCTTCGGGACAGAGATGCGCTGGAAAAAATT
     A  G  N  L  S  F  H  K  L  D  L  R  D  R  D  A  L  E  K  I 310       320       330       340       350
          |         |         |         |         |
    TTTTCTTCCACAAAGTTTGATTCTGTCATACATTTTGCTGGACTGAAAGCA
     F  S  S  T  K  F  D  S  V  I  H  F  A  G  L  K  A

SEQ ID NO: 2
```

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
      (A) LENGTH: 381 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (ix) FEATURE:
      (A) NAME/KEY: CDS
      (B) LOCATION: 85..381

(xi) SEQUENCE DESCRIPTION: SEQ ID NO: 1:

```
GAATTCCTGA AATCTGAAGT GTGAAGAAGA ATAATAATAA GGAACAGTGA G TGGGATTTG         60

AAGGGAAAGA AGAAGAAGAA GAAG ATG GTG TCG TCG AGG ATG GCG TCA GGG            111
                           Met Val Ser Ser Arg Met Ala Ser Gly
                            1               5

GAA ACA ATT CTG GTA ACT GGA GGA GCT GGA T TC ATC GGA TCT CAC ACG          159
Glu Thr Ile Leu Val Thr Gly Gly Ala Gly P he Ile Gly Ser His Thr
 10              15                  20                  25

GTG GTT CAG CTT CTG AAG CAA GGG TTT CAC G TA TCC ATC ATC GAC AAT          207
Val Val Gln Leu Leu Lys Gln Gly Phe His V al Ser Ile Ile Asp Asn
         30                  35                  40

CTC TAC AAC TCC GTC ATC GAC GCC GTC CAT A GG GTT CGC CTT TTG GTG          255
Leu Tyr Asn Ser Val Ile Asp Ala Val His A rg Val Arg Leu Leu Val
     45                  50                  55

GGT CCA CTC CTC TCC AGC AAC CTC CAT TTC C AT CAC GGC GAC CTC CGC          303
Gly Pro Leu Leu Ser Ser Asn Leu His Phe H is His Gly Asp Leu Arg
 60                  65                  70

AAC ATC CAT GAC CTC GAC ATC CTC TTC TCT A AA ACC AAA TTT GAT GCC          351
Asn Ile His Asp Leu Asp Ile Leu Phe Ser L ys Thr Lys Phe Asp Ala
     75                  80                  85
```

```
GTG ATC CAA CTT GCG GGC CCC AAA GGT GTG                          381
Val Ile Gln Leu Ala Gly Pro Lys Gly Val
 90                  95
```

(2) INFORMATION FOR SEQ ID NO: 2:

(i) SEQUENCE CHARACTERISTICS:
        (A) LENGTH: 351 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 79..351

(xi) SEQUENCE DESCRIPTION: SEQ ID NO: 2:

```
GAATTCCTTC AAAGCTATCC ATACCGCTTA CGCATTCATT CACTCCACCT T CTCTTTCTC    60

TCTCAGCTCC CTTCAATT ATG TCA TCC CAA ACG GTT CTC  GTC ACC GGC GGA   111
                   Met Ser Ser Gln Thr Val Leu Val Thr Gly Gly
                    1               5                  10

GCC GGT TAC ATC GGC AGC CAC ACC GTC CTT C AG CTT CTC CTC GGT GGT   159
Ala Gly Tyr Ile Gly Ser His Thr Val Leu G ln Leu Leu Leu Gly Gly
             15                  20                  25

TTC AAG GCC GTT GTC GTT GAC AAC CTC GAT A AT TCT TCC GAG ACC GCC   207
Phe Lys Ala Val Val Val Asp Asn Leu Asp A sn Ser Ser Glu Thr Ala
         30                  35                  40

ATC CAC AGA GTC AAG GAA CTC GCC GGT AAA T TC GCC GGT AAT CTC TCC   255
Ile His Arg Val Lys Glu Leu Ala Gly Lys P he Ala Gly Asn Leu Ser
     45                  50                  55

TTT CAC AAG TTA GAC CTT CGG GAC AGA GAT G CG CTG GAA AAA ATT TTT   303
Phe His Lys Leu Asp Leu Arg Asp Arg Asp A la Leu Glu Lys Ile Phe
 60                  65                  70                  75

TCT TCC ACA AAG TTT GAT TCT GTC ATA CAT T TT GCT GGA CTG AAA GCA   351
Ser Ser Thr Lys Phe Asp Ser Val Ile His P he Ala Gly Leu Lys Ala
                 80                  85                  90
```

(2) INFORMATION FOR SEQ ID NO: 3:

(i) SEQUENCE CHARACTERISTICS:
        (A) LENGTH: 99 amino acids
        (B) TYPE: amino acid
        (D) TOPOLOGY: linear (ii) MOLECULE TYPE: protein (xi) SEQUENCE DESCRIPTION: SEQ ID NO: 3:

```
Met Val Ser Ser Arg Met Ala Ser Gly Glu T hr Ile Leu Val Thr Gly
 1               5                  10                  15

Gly Ala Gly Phe Ile Gly Ser His Thr Val V al Gln Leu Leu Lys Gln
             20                  25                  30

Gly Phe His Val Ser Ile Ile Asp Asn Leu T yr Asn Ser Val Ile Asp
         35                  40                  45

Ala Val His Arg Val Arg Leu Leu Val Gly P ro Leu Leu Ser Ser Asn
     50                  55                  60

Leu His Phe His His Gly Asp Leu Arg Asn I le His Asp Leu Asp Ile
 65                  70                  75                  80

Leu Phe Ser Lys Thr Lys Phe Asp Ala Val I le Gln Leu Ala Gly Pro
```

-continued

```
                    85                  90                  95
Lys Gly Val (2) INFORMATION FOR SEQ ID NO: 4:

(i) SEQUENCE CHARACTERISTICS:
        (A) LENGTH: 91 amino acids
        (B) TYPE: amino acid
        (D) TOPOLOGY: linear (ii) MOLECULE TYPE: protein (xi) SEQUENCE DESCRIPTION: SEQ ID NO: 4:

Met Ser Ser Gln Thr Val Leu Val Thr Gly G ly Ala Gly Tyr Ile Gly
1               5                   10                  15

Ser His Thr Val Leu Gln Leu Leu Gly G ly Phe Lys Ala Val Val
            20                  25                  30

Val Asp Asn Leu Asp Asn Ser Ser Glu Thr A la Ile His Arg Val Lys
            35                  40                  45

Glu Leu Ala Gly Lys Phe Ala Gly Asn Leu S er Phe His Lys Leu Asp
        50                  55                  60

Leu Arg Asp Arg Asp Ala Leu Glu Lys Ile P he Ser Ser Thr Lys Phe
65                  70                  75                  80

Asp Ser Val Ile His Phe Ala Gly Leu Lys A la
                85                  90
```

What is claimed is:

1. An isolated UDP-galactose epimerase enzyme, comprising the polypeptide sequence shown as SEQ ID No. 3 or SEQ ID No. 4, or a polypeptide sequence which is at least 85% homologous to SEQ ID No. 3 or SEQ ID No. 4.

2. An isolated UDP galactose epimerase enzyme encoded by a nucleotide sequence that comprises the sequence shown as SEQ ID No. 1 or SEQ ID No. 2, or a nucleotide sequence which is at least 85% homologous to SEQ ID No. 1 or SEQ ID No. 2.

3. An isolated nucleotide sequence encoding a protein with epimerase activity that comprises the sequence shown as SEQ ID No. 1 or SEQ ID no. 2, or a sequence which is at least 85% homologous to SEQ ID No. 1 or SEQ ID No. 2, or a sequence complementary thereto.

4. A nucleotide sequence according to claim 3 operatively linked to a promoter.

5. A polynucleotide construct comprising the nucleotide sequence of claim 3.

6. A vector comprising the nucleotide sequence of claim 3.

7. A plasmid comprising the nucleotide sequence of claim 3.

8. A transgenic microorganism or plant comprising the nucleotide sequence of claim 3.

9. A process of preparing a UDP-galactose epimerase enzyme, comprising expressing a nucleotide sequence according to claim 3.

10. The UDP-galactose epimerase enzyme of claim 1, comprising the polypeptide sequence shown as SEQ ID No. 3 or SEQ ID No. 4, or a polypeptide sequence which is at least 90% homologous to SEQ ID No. 3 or SEQ ID No. 4.

11. The UDP-galactose epimerase enzyme of claim 1, comprising the polypeptide sequence shown as SEQ ID No. 3 or SEQ ID No. 4, or a polypeptide sequence which is at least 95% homologous to SEQ ID No. 3 or SEQ ID No. 4.

12. The UDP-galactose epimerase enzyme of claim 1, comprising the polypeptide sequence shown as SEQ ID No. 3 or SEQ ID No. 4, or a polypeptide sequence which is at least 98% homologous to SEQ ID No. 3 or SEQ ID No. 4.

13. The UDP-galactose epimerase enzyme of claim 2, encoded by a nucleotide sequence that comprises the sequence shown as SEQ ID No. 1 or SEQ ID No. 2, or a nucleotide sequence which is at least 90% homologous to SEQ ID No. 1 or SEQ ID No. 2.

14. The UDP-galactose epimerase enzyme of claim 2 encoded by a nucleotide sequence that comprises the sequence shown as SEQ ID No.1 or SEQ ID No. 2, or a nucleotide sequence which is at least 95% homologous to SEQ ID No. 1 or SEQ ID No. 2.

15. The UDP-galactose epimerase enzyme of claim 2 encoded by a nucleotide sequence that comprises the sequence shown as SEQ ID No. 1 or SEQ ID No. 2, or a nucleotide sequence which is at least 98% homologous to SEQ ID No. 1 or SEQ ID No. 2.

16. The nucleotide sequence of claim 3, that comprises the sequence shown as SEQ ID No. 1 or SEQ ID No. 2, or a sequence which is at least 90% homologous to SEQ ID No. 1 or SEQ ID No. 2, or a sequence complementary thereto.

17. The nucleotide sequence of claim 3, that comprises the sequence shown as SEQ ID No. 1 or SEQ ID No. 2, or a sequence which is at least 95% homologous to SEQ ID No. 1 or SEQ ID No. 2, or a sequence complementary thereto.

18. The nucleotide sequence of claim 3, that comprises the sequence shown as SEQ ID No. 1 or SEQ ID No. 2, or a sequence which is at least 98% homologous to SEQ ID No. 1 or SEQ ID No. 2, or a sequence complementary thereto.

* * * * *